(12) United States Patent
Ryu et al.

(10) Patent No.: US 9,879,236 B2
(45) Date of Patent: Jan. 30, 2018

(54) GGPS GENE FOR PROMOTING HIGHER GROWTH OR BIOMASS OF PLANT AND USE THEREOF

(75) Inventors: Beung Tae Ryu, Daejeon (KR); Kumar Tata Sandeep, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 268 days.

(21) Appl. No.: 13/878,367

(22) PCT Filed: Oct. 5, 2011

(86) PCT No.: PCT/KR2011/007351
§ 371 (c)(1),
(2), (4) Date: Apr. 8, 2013

(87) PCT Pub. No.: WO2012/047006
PCT Pub. Date: Apr. 12, 2012

(65) Prior Publication Data
US 2013/0205447 A1 Aug. 8, 2013

(30) Foreign Application Priority Data
Oct. 8, 2010 (KR) .......................... 10-2010-0098072

(51) Int. Cl.
C12N 15/82 (2006.01)
C12N 9/10 (2006.01)

(52) U.S. Cl.
CPC ......... *C12N 9/1085* (2013.01); *C12N 15/827* (2013.01); *C12N 15/8261* (2013.01); *C12Y 205/01029* (2013.01)

(58) Field of Classification Search
None
See application file for complete search history.

(56) References Cited

U.S. PATENT DOCUMENTS

| 4,940,838 A | 7/1990 | Schilperoort et al. |
| 2013/0014292 A1* | 1/2013 | Pennell .............. C12N 15/8261 800/290 |

FOREIGN PATENT DOCUMENTS

| EP | 0116718 B1 | 5/1990 |
| EP | 0120516 B1 | 10/1991 |
| KR | 10-2003-0011780 A | 2/2003 |
| KR | 10-0814941 B1 | 3/2008 |
| KR | 10-0871591 B1 | 11/2008 |
| WO | WO 99/07867 * | 2/1999 |

OTHER PUBLICATIONS

Zhu et al., Plant Mol Biol 53:331-41 (1997).*
Crane, Phil Trans Biol Sci 359(1444):735-37 (2004).*
Oh et al., J Plant Physiol 157:535-47 (2000).*
Zhang et al., Curr Opin Plant Biol 6:430-40 (2003).*
Van Camp, Curr Opin Biotech 16:147-53 (2005).*
Luo & Saltzman, Nat Biotech 18:33-37 (2000).*
Qin et al., Plant Cell Physiol 45(8):1042-52 (2004).*
Okada et al., Plant Physiol 122:1045-1056 (2000).*
International Search Report for PCT/KR2011/007351.
Kai Ament, "Induction of a leaf specific geranylgeranyl pyrophosphate synthase and emission of (E,E)-4,8,12-trimethyltrideca-1,3,7,11-tetraene in tomato are dependent on both jasmonic acid and salicylic acid signaling pathways", Planta, 2006, V.24, 1197-1208.
Jerry Hefner, "Cloning and Functional Expression of a cDNA Encoding Geranylgeranyl Diphosphate Synthase from Taxus canadensis and Assessment of the Role of this Prenyltransferase in Cells Induced for Taxol Production", Archives of Biochemistry & Biophysics, 1998, V.360, 62-74.
Chuan-yinWu , "Brassinosteroids Regulate Grain Filling in Rice", The Plant Cell, 2008, V.20, 2130-2145.
Worapan Sitthithaworn, "Geranylgeranyl Diphosphate Synthase from Scoparia dulcis and Croton sublyratus. Plastid Localization and Conversion to a Farnesyl Diphosphate Synthase by Mutagenesis", Chem. Pharm. Bull. 2001, V. 49, 197-202.
Hanahan, D., J. Mol. Biol., 166:557-580(1983).
Krens, F.A. et al., 1982, Nature 296, 72-74.
Negrutiu I. et al., Jun. 1987, Plant Mol. Biol. 8, 363-373).
Shillito R.D. et al., 1985 Bio/Technol. 3, 1099-1102).
Crossway A. et al., 1986, Mol. Gen. Genet. 202, 179-185).
Klein T.M. et al., 1987, Nature 327, 70.
Journal of Plant Physiology, 157, V5, 535-542(Nov. 2000).
NCBI database accession No. AF020041.1(Nov. 18, 1998).
Weigel & Glazebrook, Arabidopsis: A laboratory Manual. Cold Spring Harbour Laboratory Press, New York, 2002, 125-127.
Bae et al., Plant Cell Tiss Org 2005, 80:51-57.

* cited by examiner

*Primary Examiner* — Cathy Kingdon Worley
*Assistant Examiner* — Russell T Boggs
(74) *Attorney, Agent, or Firm* — The PL Law Group, PLLC

(57) ABSTRACT

A method for increasing growth or biomass of a plant in a shorter period of time, compared to a control plant, includes transforming a plant cell using a recombination vector including a geranylgeranyl pyrophosphate synthase (GGPS) gene. A method for preparing a transgenic plant having higher growth or biomass in a shorter period of time, compared to a control plant, includes transforming a plant cell using the recombination vector having the GGPS gene. A composition for promoting higher growth or biomass of a plant, compared to a plant body, includes a GGPS gene. A plant or seed of the plant having higher growth or biomass, compared to the control plant, is prepared using the method.

5 Claims, 5 Drawing Sheets

Control (GUS 1-3)    GGPS5-3

SEQUENCE LISTING

<160> NUMBER OF SEQ ID NOS: 1

<210> SEQ ID NO 1
<211> LENGTH: 1283
<212> TYPE: DNA
<213> ORGANISM: Helianthus annuus

<400> SEQUENCE: 1
atttcttctt gttacaacaa caatcaaatc aaatccactt gtccaaccat gagacccatg    60

-continued

```
agtttggttc attcatgttc catcttcacc ggatcttcat tcatcaaaac aaccccatt      120 aacaacaaac ccactttcaa gattcaccaa agacccacaa ttagatccac aatttctgca      180
gcaattgttg aagaagaagt agttgagttg caacaaaaac ccaaacccac tttcaatttc      240
aacgcttaca tgttgggaaa gggtaattct gtccataaag ctcttgatga atcaattatg      300
attaaaaacc caccaacaat acatgaagct atgaggtact ctttacttgc tggtgggaag      360
cgcgtcaggc ccattctctg tattgccgcg tgtgagctcg tcggagggga ggaggccacc      420
gccatgccgg cggcctgtgc ggtggagatg atacacacca tgtctttgat acatgatgat      480
cttccttgta tggataatga tgatttccgt agagggaagc ccactaatca taaggtttat      540
ggggaagacg ttgccgtttt ggcaggcgat tcgctgctgg cgtttgcttt cgagtatgtt      600
tctagtagga cggaaggcgc atcgcctgca cgcgtcttgg ctgccatcgg ggagctcgcc      660
aagtcgattg ggaccgaagg gctggtggca gggcaagtgg tggatattgc ttcaaccggg      720
ggccaagata tcggattgga tcagctagag tttatacaca tacataaaac cgcagcattg      780
ttggaggctt ctgttgtgtt gggagctatc ttgggtggtg ggagtgatgc gcaggtggag      840
aagctgagga cattcgcgcg gtgcatcggg ttgttgtttc aggtggtgga tgatatactt      900
gatgtgacca agtcgtccga ggaattgggg aaaaccgcag ggaaagattt gttggtggat      960
aagacgacat atccgaaact gcttgggttg gacaagtcga ggcagtttgc ggaggagttg     1020
ctggcggagg ctaaacagca gctggaggag tttgaatcgc aggcggcggt ggcgccgttg     1080
ttggctctgg cggagtatat agcttaccgc cagaactaat gttgttgtat tgtaacctag     1140
gttgctgttg tcatcaattt gattcatacc tgtttgatga tgtaagatta attgacttga     1200
agaaacagga ggcaaattag attttctttt tgattgcaat ataccaccta tattatcatt     1260
ctgaaaaaaa aaaaaaaaaa aaa                                            1283
```

GGPS GENE FOR PROMOTING HIGHER GROWTH OR BIOMASS OF PLANT AND USE THEREOF

CROSS REFERENCE TO RELATED APPLICATIONS AND CLAIM OF PRIORITY

This patent application is a National Phase application under 35 U.S.C. § 371 of International Application No. PCT/KR2011/007351, filed Oct. 5, 2011, which claims priority to Korean Patent Application No. 10-2010-0098072 filed Oct. 8, 2010, entire contents of which are incorporated herein by reference.

BACKGROUND

1. Technical Field

The present invention relates to a GGPS gene for inducing fast growth or fast biomass increase of plant and its use. More specifically, the present invention relates to a method for inducing fast growth or fast biomass increase of plant compared to control plant by transforming a plant cell with the recombinant vector containing GGPS (geranylgeranyl pyrophosphate synthase) gene, a method for producing a transgenic plant with induced fast growth or fast biomass increase compared to a control plant including transforming a plant cell with the recombinant vector containing GGPS gene, a plant and a seed with induced fast growth or fast biomass increase compared to a control plant produced by the method, and a composition for inducing fast growth or fast biomass increase of plant compared to control plant including the GGPS gene.

2. Description of the Related Art

The necessity of research for increasing efficiency of agriculture due to global population increase and arable land reduction useful for agriculture is on the rise. Also, Korea depends on import from USA, China and the like a lot for major crop plants such as corn, wheat, soybean and the like, and import amount of farm products is several fold of its export amount. Development of plant biotechnology provides crops or plants with enhanced economic, agricultural and horticultural traits, and development of transgenic plant with enhanced growth rate (fast biomass increase) can be an alternative for compensating the reduced crop resources.

Research and development of transgenic plant for increasing plant yield up to now was progressed a lot. Various transgenic plants with increased growth and biomass using genes from various plants (corn, soybean, hot pepper, *Arabidopsis*, tobacco or rice and the like) or microorganisms (*Synechocystis, Pseudomonas, Bacillus* or *Anabaena* and the like) were reported.

GGPS (geranylgeranyl pyrophosphate synthase) is known as an enzyme catalyzing production reaction of GGPP (geranylgeranyl pyrophosphate) from FPP (farnesyl pyrophosphate), an intermediate of HMG-CoA reductase pathway and the GGPP produced in the reaction becomes a precursor of cartenoid having antioxidant activity.

According to Korean Patent Registration No. 10-0814941, a method for mass production of lycopene, a kind of carotenoid from *E. coli* transformed with GGPS gene is described. Furthermore, according to Korean Patent Registration No. 10-0871591, a method for producing transgenic plant with increased biomass using CaPLA1 gene from hot pepper is described. Furthermore, according to Korean Patent Publication No. 2003-0011780, a method for producing transgenic plant with increased seed yield and biomass using SH2-REV6-HS gene from corn is described.

SUMMARY

The present invention is devised in view of the above-described needs. The inventors of the present invention confirmed that faster growth or faster biomass increase compared to control plant in tobacco plant transformed with the GGPS gene from *Helianthus annuus* is induced and therefore completed the invention.

In order to solve the problems described above, the present invention provides a method for inducing fast growth or fast biomass increase of plant compared to control plant by transforming a plant cell with the recombinant vector containing GGPS (geranylgeranyl pyrophosphate synthase) gene.

Further, the present invention provides a method for producing a transgenic plant with induced fast growth or fast biomass increase compared to a control plant including transforming a plant cell with the recombinant vector containing GGPS gene.

Further, the present invention provides a plant and a seed with induced fast growth or fast biomass increase compared to a control plant produced by the method.

Further, the present invention provides a composition for inducing fast growth or fast biomass increase of plant compared to control plant including the GGPS gene.

Since a plant with induced fast growth or fast biomass increase compared to a control plant using the GGPS gene from *Helianthus annuus* can be produced, it can be useful to solve supply reduction problem of crop resources if applied to crop plant.

DETAILED DESCRIPTION

Figure 1:
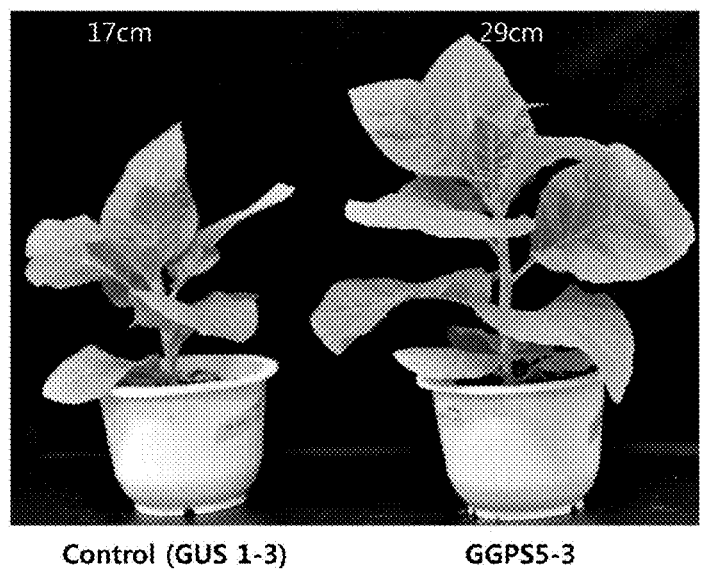
FIG. 1 is a photograph showing fast growth of GGPS-transgenic tobacco lines ($T_1$) compared to the control GUS-transgenic tobacco lines ($T_1$).

In order to achieve the purpose of the invention described as above, the present invention provides a method for inducing fast growth or fast biomass increase of plant compared to control plant, including transforming a plant cell with the recombinant vector containing GGPS (geranylgeranyl pyrophosphate synthase) gene to overexpress the GGPS gene.

In an embodiment of the present method, the fast growth or fast biomass increase of plant may be increase of plant growth rate, fast height and weight increase, induction of early flowering, increase of seed yield, or increase of number of flower, but not limited thereto.

Preferably, the GGPS gene can be derived from *Helianthus annuus*, but a gene source is not limited to *Helianthus annuus*. The GGPS gene of the present invention includes both genomic DNA and cDNA which encode the GGPS protein. Preferably, the gene of the present invention may include the nucleotide sequence represented by SEQ ID NO: 1. Further, variants of said nucleotide sequence are also within the scope of the present invention. Specifically, said gene may include a nucleotide sequence with at least 70%, preferably at least 80%, more preferably at least 90%, and still more preferably at least 95% identity with the nucleotide sequences of SEQ ID NO: 1. The "sequence identity %" for a certain polynucleotide is determined by comparing two nucleotide sequences that are optimally arranged with a region to be compared. In this regard, a part of the polynucleotide sequence in a region to be compared may include an addition or a deletion (i.e., a gap) compared to a reference sequence (without any addition or deletion) relative to the optimized arrangement of the two sequences.

The term "recombinant" indicates a cell which replicates a heterogeneous nucleotide or expresses said nucleotide, a peptide, a heterogeneous peptide, or a protein encoded by a heterogeneous nucleotide. Recombinant cell can express a gene or a gene fragment in a form of a sense or antisense, which is not found in natural state of cell. In addition, a recombinant cell can express a gene that is found in the natural state, provided that said gene is modified and re-introduced into the cell by an artificial means.

In the present invention, the GGPS DNA sequence can be inserted into a recombinant expression vector. The term "recombinant expression vector" means bacterial plasmid, phage, yeast plasmid, plant cell virus, mammalian cell virus, or other vectors. Altogether, any plasmid and vector can be used provided that they are capable of replicating and stabilizing in the host. An important feature of the expression vector is having a replication origin, a promoter, a marker gene, and a translation control element.

An expression vector containing GGPS DNA sequence and appropriate transcription/translation control signals can be constructed using methods well known to those skilled in the art. These methods include in vitro recombinant DNA techniques, DNA synthesis techniques, in vivo recombinant techniques, and the like. Said DNA sequence can be effectively linked to an appropriate promoter in the expression vector in order to direct mRNA synthesis. An expression vector may also include a ribosome binding site as a translation initiation site and a transcription terminator.

A preferred example of the recombinant vector is Ti-plasmid vector which can transfer a part of itself, i.e., so-called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a plant genome. Especially preferred form of Ti-plasmid vector is a so-called binary vector which has been disclosed in EP 0 120 516 B1 and U.S. Pat. No. 4,940,838. Other appropriate vectors that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be especially advantageous when a plant host cannot be appropriately transformed. Preferably, the recombinant vector can be pBI101 vector, but not limited thereto.

Expression vector preferably includes at least one selection marker. Said selection marker is a nucleotide sequence having a property which allows a selection based on a common chemical method. Any kind of gene that can be used for the differentiation of transformed cells from non-transformed cells can be a selection marker. Example includes, a gene resistant to herbicide such as glyphosate and phosphinotricin, and a gene resistant to antibiotics such as kanamycin, G418, bleomycin, hygromycin, and chloramphenicol, but not limited thereto.

According to the recombinant vector of the present invention, the promoter can be CaMV 35S promoter, actin promoter, ubiquitin promoter, pEMU promoter, MAS promoter, or histone promoter, but not limited thereto. The term "promoter" indicates a region of DNA located upstream of a structure gene, and it corresponds to a DNA molecule to which an RNA polymerase binds to initiate transcription. The term "plant promoter" indicates the promoter that can initiate transcription in a plant cell. The term "constitutive promoter" indicates the promoter that is active under most environmental conditions and cell growth or differentiation state. Since selection of a transformant can be made for various tissues at various stages, the constitutive promoter may be preferred for the present invention. Thus, selection property is not limited by a constitutive promoter.

In the above-described recombinant vector of the invention, any kind of a typical terminator can be used. Example includes, nopalin synthase (NOS), rice α-amylase RAmy1 A terminator, phaseoline terminator, and a terminator for Octopine gene of *Agrobacterium tumefaciens*, etc., but are not limited thereto. Regarding the necessity of terminator, it is generally known that such region can increase a reliability and an efficiency of transcription in plant cells. Therefore, the use of terminator is highly preferable in view of the context of the present invention.

Any kind of a host cell known in the pertinent art can be used if stable and continuous cloning and expression of the vector of the present invention can be achieved in prokaryotic cells by using it. Examples include strains belonging to the genus *Bascillus* such as *E. coli* JM109, *E. coli* BL21, *E. coli* RR1, *E. coli* LE392, *E. coli* B, *E. coli* X 1776, *E. coli* W3110, *Bascillus subtilus*, *Bascillus thuringiensis*, and the like, *Salmonella typhimurium*, intestinal flora and strains such as *Serratia marcescens* and various *Pseudomonas* Spp. and the like.

In addition, when the vector of the present invention is transformed in an eukaryotic cell, a host cell such as *Saccharomyce cerevisiae*, an insect cell, a human cell (e.g., CHO cell line (Chinese hamster ovary), W138, BHK, COS-7, 293, HepG2, 3T3, RIN and MDCK cell line), a plant cell line and the like can be used. Preferably, the host cell is a plant cell.

When a host cell is a prokaryotic cell, transfer of the vector of the present invention into a host cell can be carried out according to the CaCl$_2$ method, the Hanahan's method (Hanahan, D., J. Mol. Biol., 166:557-580(1983)), and an electroporation method, etc. In addition, when a host cell is an eukaryotic cell, the vector of the present invention can be transferred into a host cell according to a microscopic injection method, a calcium phosphate precipitation method, an electroporation method, a liposome-mediated transformation, a DEAE-dextran treatment method and a gene bombardment method, etc.

Plant transformation means any method by which DNA is delivered to a plant. Such transformation method does not necessarily have a period for regeneration and/or tissue culture. Transformation of plant species is now quite general not only for dicot plants but also for monocot plants. In principle, any transformation method can be used for introducing a hybrid DNA of the present invention to an appropriate progenitor cells. It can be appropriately selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method for plant components (Crossway A. et al., 1986, Mol. Gen. Genet. 202, 179-185), a particle bombardment method for various plants components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. A method preferred in the present invention includes *Agrobacterium* mediated DNA transfer. In particular, so-called binary vector technique as disclosed in EP A 120 516 and U.S. Pat. No. 4,940,838 can be preferably adopted for the present invention.

Further, the present invention provides a method for producing a transgenic plant with induced fast growth or fast biomass increase compared to a control plant, including transforming a plant cell with the recombinant vector containing GGPS (geranylgeranyl pyrophosphate synthase) gene, and regenerating the transformed plant cell into a transgenic plant.

The method of the present invention includes a step of transforming a plant cell with the recombinant vector of the present invention, and such transformation may be mediated by *Agrobacterium tumefaciens*. In addition, the method of the present invention includes a step of regenerating a transformed plant cell to a transgenic plant. A method of regenerating a transformed plant cell to a transgenic plant can be any method that is well known in the pertinent art. In an embodiment of the present method, the GGPS gene is described as above.

The transformed plant cell must be regenerated into whole plant. The technique for regeneration from callus or protoplast culture to a mature plant is well known in the art for a number of species.

Further, the present invention provides a plant and its seed with induced fast growth or fast biomass increase compared to a control plant that is transformed with the recombinant vector including GGPS gene. Preferably, the GGPS gene may consists of SEQ ID NO: 1. Preferably, the plant may be dicot plant, but not limited thereto.

The dicot plant may be Diapensiaceae, Clethraceae, Pyrolaceae, Ericaceae, Myrsinaceae, Primulaceae, Plumbaginaceae, Ebenaceae, Styracaceae, Symplocaceae, Symplocaceae, Oleaceae, Loganiaceae, Gentianaceae, Menyanthaceae, Apocynaceae, Asclepiadaceae, Rubiaceae, Polemoniaceae, Convolvulaceae, Boraginaceae, Verbenaceae, Labiatae, Solanaceae, Scrophulariaceae, Bignoniaceae, Acanthaceae, Pedaliaceae, Orobanchaceae, Gesneriaceae, Lentibulariaceae, Phrymaceae, Plantaginaceae, Caprifoliaceae, Adoxaceae, Valerianaceae, Dipsacaceae, Campanulaceae, Compositae, Myricaceae, Juglandaceae, Salicaceae, Betulaceae, Fagaceae, Ulmaceae, Moraceae, Urticaceae, Santalaceae, Loranthaceae, Polygonaceae, Phytolaccaceae, Nyctaginaceae, Aizoaceae, Portulacaceae, Caryophyllaceae, Chenopodiaceae, Amaranthaceae, Cactaceae, Magnoliaceae, Illiciaceae, Lauraceae, Cercidiphyllaceae, Ranunculaceae, Berberidaceae, Lardizabalaceae, Menispermaceae, Nymphaeaceae, Ceratophyllaceae, Cabombaceae, Saururaceae, Piperaceae, Chloranthaceae, Aristolochiaceae, Actinidiaceae, Theaceae, Guttiferae, Droseraceae, Papaveraceae, Capparidaceae, Cruciferae, Platanaceae, Hamamelidaceae, Crassulaceae, Saxifragaceae, Eucommiaceae, Pittosporaceae, Rosaceae, Leguminosae, Oxalidaceae, Geraniaceae, Tropaeolaceae, Zygophyllaceae, Linaceae, Euphorbiaceae, Callitrichaceae, Rutaceae, Simaroubaceae, Meliaceae, Polygalaceae, Anacardiaceae, Aceraceae, Sapindaceae, Hippocastanaceae, Sabiaceae, Balsaminaceae, Aquifoliaceae, Celastraceae, Staphyleaceae, Buxaceae, Empetraceae, Rhamnaceae, Vitaceae, Elaeocarpaceae, Tiliaceae, Malvaceae, Sterculiaceae, Thymelaeaceae, Elaeagnaceae, Flacourtiaceae, Violaceae, Passifloraceae, Tamaricaceae, Elatinaceae, Begoniaceae, Cucurbitaceae, Lythraceae, Punicaceae, Onagraceae, Haloragaceae, Alangiaceae, Cornaceae, Araliaceae or Umbelliferae(Apiaceae), but not limited thereto.

Further, the present invention provides a composition for inducing fast growth or fast biomass increase of plant compared to control plant including GGPS gene of the present invention. Said GGPS gene may preferably have a nucleotide sequence of SEQ ID NO: 1. The composition of the present invention includes the GGPS gene as effective component and fast growth or fast biomass increase of plant compared to a control plant can be induced by transforming a plant with the GGPS gene. The plant is described as above.

The present invention will now be described in greater detail with reference to the following examples. However, it is only to specifically exemplify the present invention and in no case the scope of the present invention is limited by these examples.

Plant Material

In vitro grown tobacco plants (*Nicotiana tabacum xanthi*) growing on Murashige and Skoog (1962) (MS)-based medium with 3% (w/v) sucrose and 0.3% (w/v) phytagel in plastic jars were obtained from Prof Jeong Sheop Shin of Korea University. The plants were maintained under long day conditions consisting of 16 hours of light with a light intensity of 20 $\mu$molm$^{-2}$ s$^{-1}$ from 40 W cool white and red deluxe fluorescent tubes (1:1 mix) and 8 hours of darkness at 23° C. for 1-2 months. Explants (ca. 0.5 cm in diameter) were aseptically excised from leaves of tobacco grown in vitro for transformation.

Regeneration of Leaf Explants

For shooting, excised leaf explants were individually transferred to 9 cm petri dishes with 30 ml culture medium including Murashige-Skoog (MS) salts with 3% sucrose, 1% maltose, 2 mg/l 6-benzyladenine (BA), 0.2 mg/l naphthaleneacetic acid (NAA) and 0.2% phytagel, pH 5.8. To determine the effect of growth regulators, MS medium was modified in combination of NAA (0.2 and 0.5 mg/l) and keeping the BA concentration content (2 mg/l).

These hormonal compositions were based on tissue culture experiments on Russian dandelion (Bae et al., Plant Cell Tiss Org 2005, 80:51-57). Culture conditions were maintained at 23±1° C. under a 16-h photoperiod with light intensity of 20 µmolm$^{-2}$ s$^{-1}$ in 40 W cool white and red deluxe fluorescent tubes (1:1 mix). For rooting, leaf explants with adventitious shoots were incubated in medium containing ½ MS salts with 1.5% sucrose, 0.05 mg/l NAA, and 0.2% phytagel, pH 5.8.

Transformation of GV3101 with pBI121 Containing GGPS and GUS Gene Separately

*Agrobacterium tumefaciens* strain GV3101 carrying a derivative of the plasmid pBI121 one harboring β-glucuronidase (GUS) and the other harboring GGPS separately were isolated following the freeze and thaw method (Weigel and Glazebrook, *Arabidopsis*: A laboratory Manual. Cold Spring Harbour Laboratory Press, New York, 2002, 125-127). GGPS gene was amplified from *Helianthus annus* cDNA library and cloned into Xba I and BamH I sites of the pBI121 vector under the CaMV 35S promoter. As control, pBI121 containing GUS (β-glucuronidase) was used. *Agrobacterium* GV3101 transformants harboring pBI121 plasmids with GGPS and GUS genes separately were screened on solid YEP medium containing 50 mg/l rifampicin and 50 mg/l kanamycin. The transformation of plasmids into *Agrobacterium* GV3101 was confirmed by PCR using GGPS-specific primers after plasmids were isolated from kanamycin-resistant GV3101 colonies.

*Agrobacterium*-Mediated Transformation Protocol (Bae et al., Plant Cell Tiss Org 2005, 80:51-57)

1. Leaf explants were excised from tobacco seedlings that were grown in vitro and incubated in a pre-culture medium (MS salts, 3% sucrose, 1% glucose, 0.2 mg/l NAA, 2.0 mg/l BA, 50 mg/l betaine, 0.3% phytagel and 0.1 mM acetosyringone, pH 5.2) for 6 days in light.

2. *Agrobacterium* were cultured overnight in 50 ml yeast-extract peptone (YEP) medium containing 100 mg/l kanamycin and 50 mg/l rifampicin at 28° C. until an OD600 nm value of 0.6-0.8.

3. The overnight culture were centrifuged, and the pellet were suspended in 50 ml induction solution (½ MS salts, 3% sucrose, 1% glucose, 50 mg/l betaine, 0.5 g/l MES, and 0.1 mM acetosyringone, pH 5.2) for 1 hour at 28° C.

4. Pre-cultured tobacco leaf explants were immersed in final bacterium culture for 15 min at room temperature with mild shaking, briefly dried on autoclaved paper, and were cultured in the dark for 3 days at 25° C. on co-culture medium (MS salts, 3% sucrose, 1% glucose, 50 mg/l betaine, 0.2 mg/l NAA, 2.0 mg/l BA, 0.3% phytagel, and 0.2 mM acetosyringone, pH 5.2) and used induction solution to wet the filter paper to cover the explants so that it remains moist 5. Following washing with washing solution (½ MS salts, 1.5% sucrose, 0.25 g/l ascorbic acid and 250 mg/l cefotaxim, pH 5.8), explants were transferred to shoot induction medium (MS salts, 3% sucrose, 1% maltose, 0.2 mg/l NAA, 2 mg/l BA, 0.3% phytagel, and 250 mg/l cefotaxim, pH 5.8)

6. After 1 week, explants were incubated in shoot induction medium containing 100 mg/l kanamycin for selective regeneration.

7. Explants were transferred to fresh selection medium biweekly for 3-5 weeks.

8. Explants with shoots were transferred to root induction medium (½ MS salts, 1.5% sucrose, 0.05 mg/l NAA, 0.2% phytagel, pH 5.8, 250 mg/l cefotaxim) containing 100 mg/l kanamycin.

9. After root formation, plants were transferred to soil for hardening for three weeks and then finally transferred to the green house.

Cultivation of Transgenic Plants

Transgenic plants were transferred to the green house and covered with polyethene (with several holes) for one week to prevent water loss. The plants were allowed to grow for 2-weeks then iron supports were given to make the plants grow erect. The plants were watered well to make them grow healthy. Regular visit to green house were made to collect the data about number of flowers, time of flowering, height, biomass and seed yield. Upon maturation, seeds were collected and the plants were harvested.

The seeds were collected and dried for a week at 28° C. Also the harvested plants were dried at 65° C. for 10 days to know the biomass yield. The seeds collected were treated with 10% (v/v) sodium hypochlorite+0.05% (v/v) tween-20 for 20 min and washed five times with autoclaved water. The seeds were germinated on MS media containing kanamycin (100 mg/l) and kept in dark at 4° C. for 3 days and then the plants were maintained under long day conditions consisting of 16 hours of light with a light intensity of 20 µmolm$^{-2}$ s$^{-1}$ from 40 W cool white and red deluxe fluorescent tubes (1:1 mix) and 8 hours of darkness at 23° C. for 15 days. The healthy plants were selected from the media and were transferred to the soil. The plants were allowed to grow in a healthy condition in green house and the data were collected upon regular visit to the green house.

Homo Line Selection

Transgenic tobacco plants ($T_0$ generation) were further selected to have $T_2$ homo lines in the kanamycin selection media. Phenotypic characteristics were observed throughout all the generation plants of $T_0$, $T_1$, and $T_2$.

Example 1: Transformation and Regeneration of Tobacco

Using *Agrobacterium*-mediated method three independent transgenic lines of tobacco were generated for the transgene-GGPS. Combination of NAA (0.2, 0.5 mg/l) with a fixed concentration of BA (2.0 mg/l) was studied to determine the ability to induce adventitious shoots. Based on the percentage of explants displaying shoot formation and regenerated leaf morphology, a combination of 2 mg/l BA and 0.2 mg/l NAA was the most suitable for shoot regeneration of tobacco. Root regeneration was significantly induced in MS media containing 0.05 mg/l NAA without any cytokinin. The transformation efficiency varied from 20 to 50%. Regenerated shoots were transferred to root induction medium containing 100 mg/l kanamycin. Rooting of these shoots was observed after 1 month. The rooting percentage was approximately 90%. The rooted plants were washed under running water and were potted in soil for acclimatization and strong development of root system under long day conditions consisting of 16 hours of light with a light intensity of 20 µmolm$^{-2}$ s$^{-1}$ from 40 W cool white and red deluxe fluorescent tubes (1:1 mix) and 8 hours of darkness at 23° C. for 45 days. After 45 days we could see a well developed rooting system in the plants which were subsequently transferred to the green house.

Example 2: Fast Increase in Plant Height and Biomass of GGPS-Transgenic Tobacco Compared to Control (GUS-Transgenic Tobacco) and Wild Type (Non-Transgenic) Plants Transgenic tobacco overexpressing GGPS gene exhibited increased overall growth and development when compared to the control tobacco plants.

Figure 2:
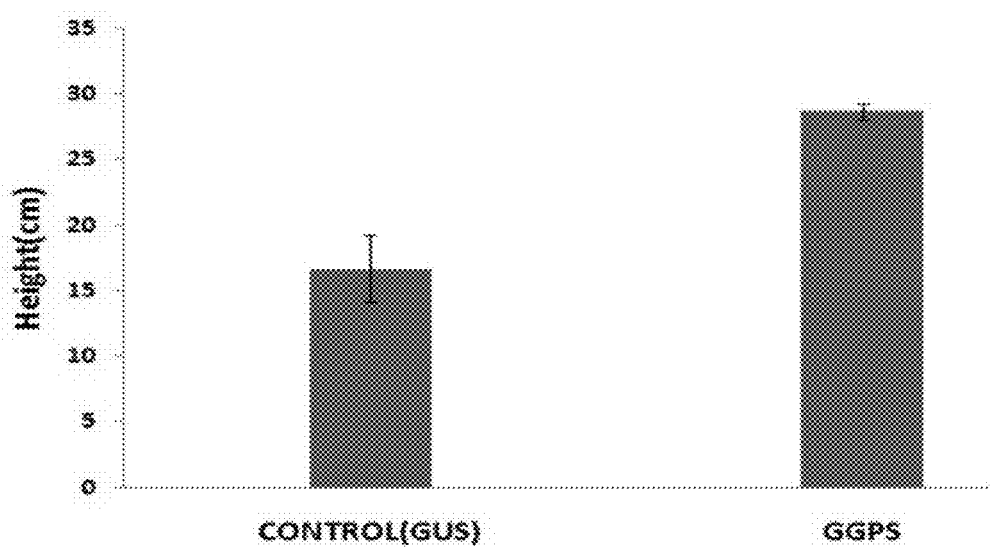
FIG. 2 is a graph in which GGPS-transgenic tobacco lines ($T_1$) shows fast growth (72% higher height) than the control GUS-transgenic tobacco lines ($T_1$).
Figure 5:
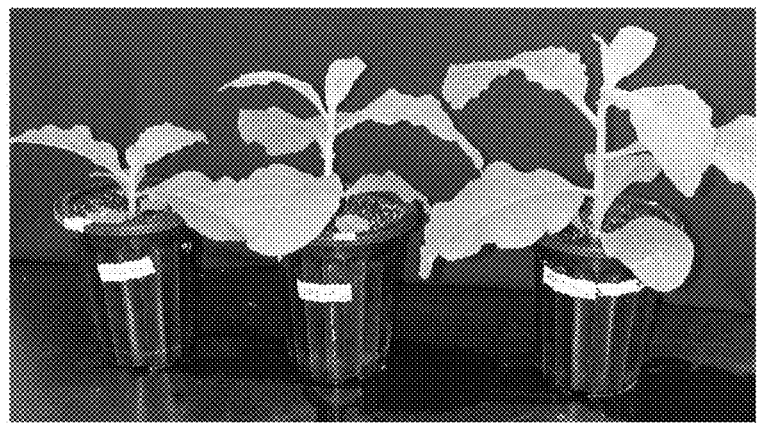
FIG. 5 is a photograph showing fast increase in the plant height and biomass of GGPS-transgenic tobacco lines ($T_2$) compared to the wild type (non-transgenic) and the control (IPP isomerase; IPPi-$T_2$) tobacco plants.

GGPS-$T_1$-transgenic plants showed fast growth (72% higher height) than the GUS-$T_1$-transgenic plants (Table 1, FIG. 2). It is evident that the transgenic GGPS-$T_1$-lines of tobacco have a lot more height (29 cm) when compared to GUS-$T_1$-line (17 cm) (FIG. 1). The same phenomena also holds good for the $T_2$ transgenic tobacco lines (FIG. 5). As the value of p is very less (p=0.0013, Table 1), our data is very much significant.

TABLE 1

Comparison of heights for control and GGPS-transgenic tobacco plants

| plant | height(cm)/plant |
|---|---|
| control(GUS) | 16.67 ± 2.52 |
| GGPS-4,5,6 lines($T_1$) | 28.67 ± 0.58 |

* t-test (p = 0.0013), (Age-50 days)

Figure 3:
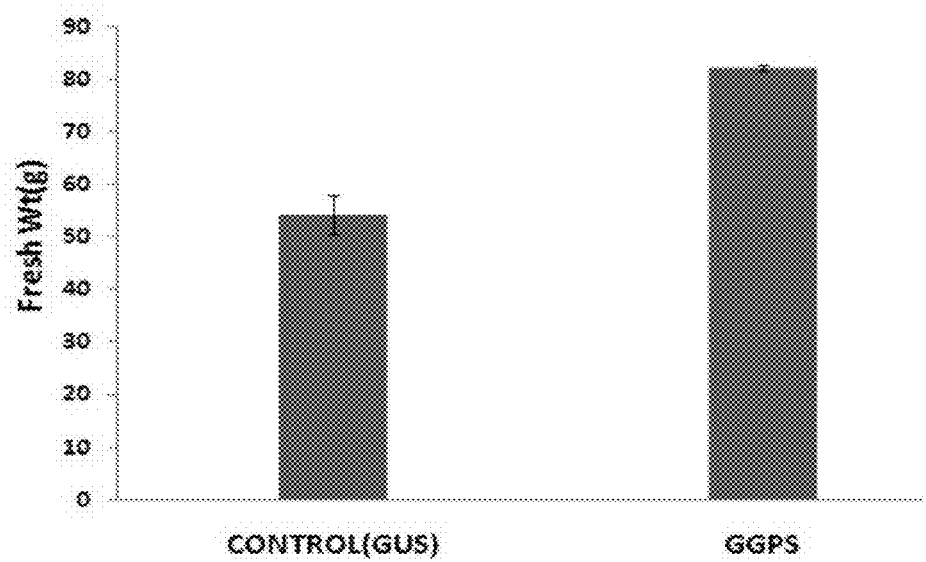
FIG. 3 is a graph in which GGPS-transgenic tobacco lines ($T_1$) shows higher growth (51% more fresh biomass) than the control GUS-transgenic tobacco lines ($T_1$).
Figure 4:
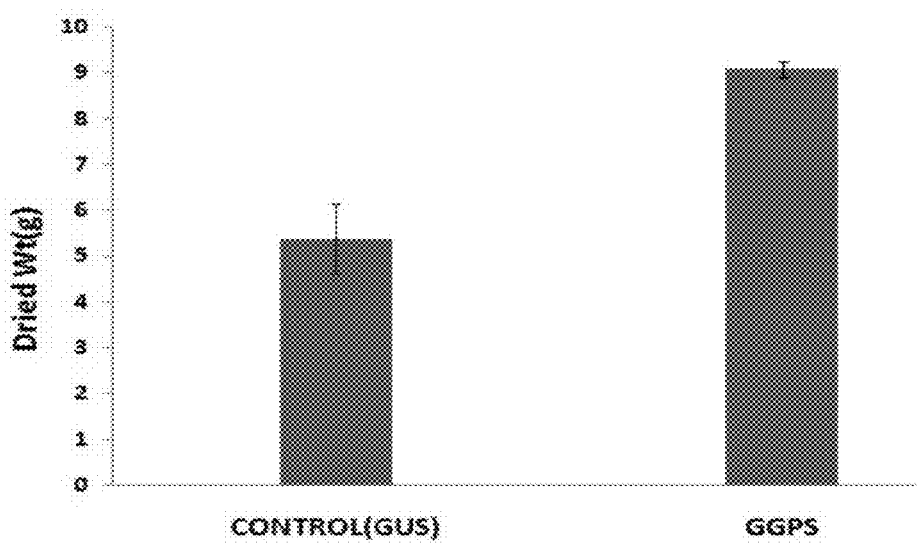
FIG. 4 is a graph in which GGPS-transgenic tobacco lines ($T_1$) shows higher growth (69% more dried biomass) than the control GUS-transgenic tobacco lines.

When comparing the fresh and dried biomass of transgenic-GGPS-$T_1$-lines and control (GUS-$T_1$-lines), transgenic-GGPS-$T_1$-lines showed 51% more fresh biomass (Table 2, FIG. 3) and 69% more dried biomass (Table 3, FIG. 4) when compared to the control tobacco plants. The data related to fresh as well as dried biomass comparison are highly significant as the p value in each case is very small.

TABLE 2

Comparison of fresh biomass for control and transgenic tobacco plants

| plant | Fresh Wt(g)/plant |
|---|---|
| control(GUS) | 54.18 ± 3.64 |
| GGPS-4,5,6 lines ($T_1$) | 82.04 ± 0.55 |

* t-test (p = 0.008), (Age-50 days)

TABLE 3

Comparison of dried biomass for control and transgenic tobacco plants

| plant | dried wt(g)/plant |
|---|---|
| control(GUS) | 5.38 ± 0.76 |
| GGPS-4,5,6 lines ($T_1$) | 9.08 ± 0.16 |

* t-test (p = 0.021), (Age-50 days)

Wild type (non-transgenic) tobacco plant and GGPS-transgenic tobacco lines ($T_2$) were planted in soil (bed soil:perlite:vermiculite:peat=4:2:1:1) in greenhouse, and then measured their growth after 5 weeks. As a result, it was confirmed that GGPS-transgenic tobacco plant has approximately 2 fold increase in growth and biomass compared to the wild type (non-transgenic) tobacco plant (FIG. 5).

GGPS-transgenic tobacco line ($T_2$) compared to control IPPi (IPP isomerase)-transgenic tobacco line ($T_2$) showed clear plant growth promotion (FIG. 5). IPPi gene promotes isomerization process of IPP (isopentenyl pyrophosphate) to DMAPP (dimethylallyl pyrophosphate) and locates in upstream compared to GGPS in the same isoprenoid compound synthesis pathway.

Example 3: Number of Seed Pods/Flower and Flowering Time

In addition to fast increases in plant height and biomass of GGPS-transgenic lines, we also examined the effect of GGPS on number of seed pods/flower and flowering time. Flowering time was determined when the first floral bud was visible and the first flower opened.

Figure 6:
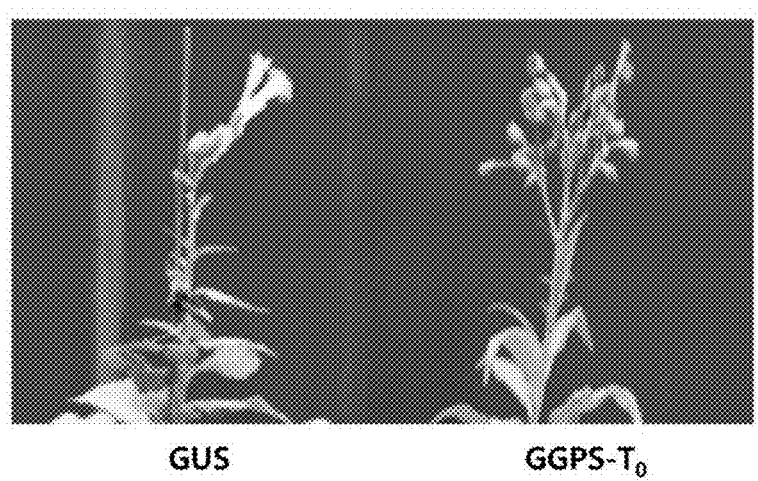
FIG. 6 is a photograph showing number of seed pods increased 4-fold in GGPS-transgenic tobacco lines ($T_0$) than the control GUS-transgenic tobacco lines ($T_0$).

When compared to the control (GUS-transgenic) tobacco lines, the number of seeds/flowers increased four-fold in GGPS-transgenic tobacco ($T_1$) (Table 4, FIG. 6). As the p value is very smaller (p=0.003), the data is highly significant.

TABLE 4

Comparison of number of seed pods/flower in control and transgenic tobacco plants

| plant | seed pods/plant |
|---|---|
| control(GUS) | 2.67 ± 2.52 |
| GGPS lines ($T_1$) | 12.67 ± 4.62 |

* t-test (p = 0.0030), pot size: 2.5 liters

Figure 8:
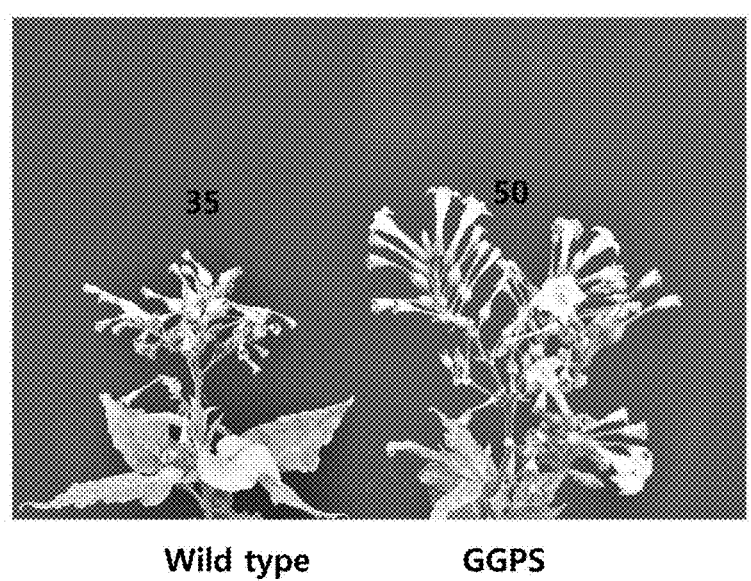
FIG. 8 is a photograph showing increased number of seed pods/flowers in GGPS-transgenic tobacco lines ($T_0$) compared to the wild type (non-transgenic) tobacco plants.
Figure 9:
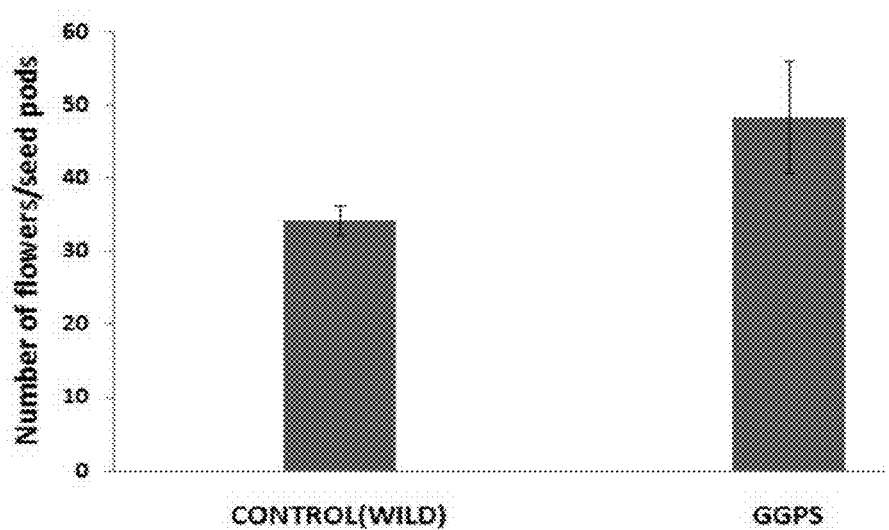
FIG. 9 is a graph in which number of seed pods is increased 41% in GGPS-transgenic tobacco lines ($T_0$) lines than the wild type (non-transgenic) tobacco plants.
Figure 10:
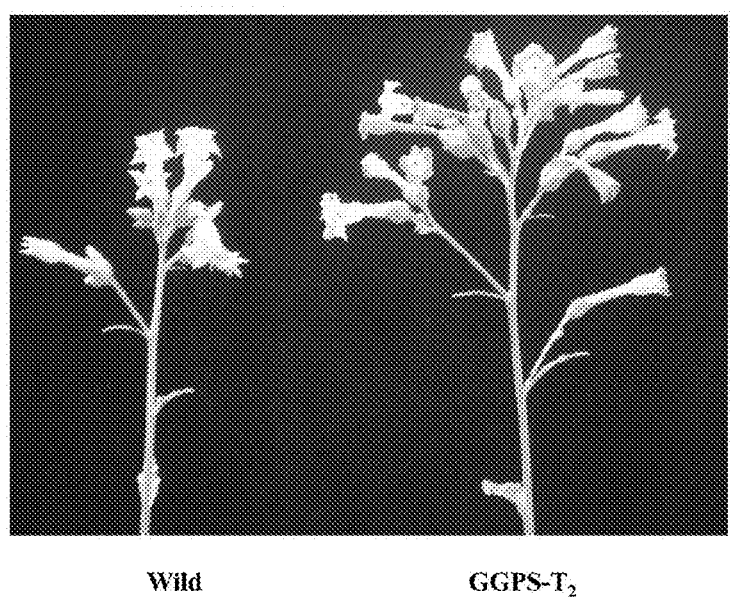
FIG. 10 is a photograph showing increased number of seed pods/flowers in GGPS-transgenic tobacco lines ($T_2$) compared to wild type (non-transgenic) tobacco plants.

A similar phenomenon of increase in the number of seed pods/flowers could be observed for $T_0$ and $T_2$ GGPS-transgenic tobacco lines (FIG. 8 and FIG. 10). $T_0$-GGPS-transgenic lines showed 41% more number of flowers/seed pods when compared to wild type (non-transgenic) lines (Table 5, FIG. 9).

TABLE 5

Comparison of number of seed pods/flower in wild type(non-transgenic) and transgenic tobacco plants

| plant | seed pods/plant |
|---|---|
| wild type | 34.3 ± 2.08 |
| GGPS lines ($T_0$) | 48.33 ± 7.64 |

* t-test (p = 0.056), (Age-75 days), pot size: 7.5 liters

Figure 7:
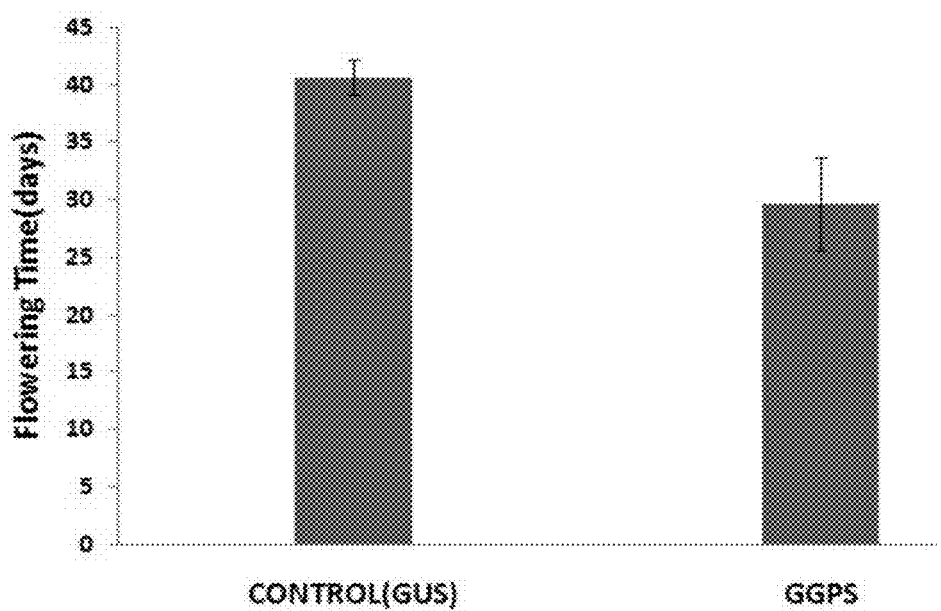
FIG. 7 is a graph in which Flowering Time is reduced (25% shorter) in GGPS-transgenic tobacco lines ($T_1$) as compared to the control GUS-transgenic tobacco lines ($T_1$).

It was observed that the growing time required for flowering was reduced in GGPS-$T_1$-transgenic tobacco plants compared to the control GUS-$T_1$-transgenic tobacco plants (FIG. 7). We could see that transgenic plants required 25% shorter period to flower than the control plants.

What is claimed is:

1. A method for inducing faster growth or faster biomass increase of a plant, compared to a control plant, the method comprising:
    transforming a plant cell with a recombinant vector containing a GGPS (geranylgeranyl pyrophosphate synthase) gene having the nucleotide sequence of SEQ ID NO: 1 to overexpress the GGPS gene;
    regenerating the transformed plant cell into a transgenic plant; and
    selecting a plant that has at least a 51% increase in fresh biomass at the age of 50 days relative to a control plant,
    wherein the plant is a dicot plant.

2. The method according to claim 1, characterized in that the faster growth or faster biomass increase of the plant is an increase of plant growth rate, a faster height increase, an induction of earlier flowering, an increase of seed yield, or an increase in flower number.

3. The method according to claim 1, wherein the selecting comprises selecting the plant that has a 51% increase in fresh biomass at the age of 50 days relative to a control plant.

4. A method for inducing faster growth or faster biomass increase of a plant, compared to a control plant, the method comprising:
    transforming a plant cell with a recombinant vector containing a GGPS (geranylgeranyl pyrophosphate synthase) gene having the nucleotide sequence of SEQ ID NO: 1 to overexpress the GGPS gene;
    regenerating the transformed plant cell into a transgenic plant; and
    selecting a plant that has at least a 69% increase in dried biomass at the age of 50 days, wherein the plant is a dicot plant relative to a control plant.

5. The method according to claim 4, wherein the selecting comprises selecting the plant that has a 69% increase in dried biomass at the age of 50 days relative to a control plant.

* * * * *

UNITED STATES PATENT AND TRADEMARK OFFICE
CERTIFICATE OF CORRECTION

PATENT NO. : 9,879,236 B2  
APPLICATION NO. : 13/878367  
DATED : January 30, 2018  
INVENTOR(S) : Beung Tae Ryu et al.

Page 1 of 1

It is certified that error appears in the above-identified patent and that said Letters Patent is hereby corrected as shown below:

On the Title Page

Item (54) and the Specification, at Column 1, Lines 1-3, the title should read as follows:
GGPS gene inducing fast growth or fast biomass increase of plant and uses thereof Signed and Sealed this
Thirteenth Day of November, 2018

Andrei Iancu
*Director of the United States Patent and Trademark Office*